United States Patent [19]
Rheinish et al.

[11] Patent Number: 5,405,386
[45] Date of Patent: Apr. 11, 1995

[54] INTRAOCULAR LENS WITH IMPROVED CYLINDRICAL HAPTIC

[75] Inventors: Robert S. Rheinish, Huntington Beach; Thomas P. Richards, Los Angeles, both of Calif.

[73] Assignee: Kabi Pharmacia Ophthalmics, Inc., Monrovia, Calif.

[21] Appl. No.: 89,044

[22] Filed: Jul. 9, 1993

[51] Int. Cl.⁶ .................................................. A61F 2/16
[52] U.S. Cl. ............................................................ 623/6
[58] Field of Search ............................................... 623/6

[56] References Cited

U.S. PATENT DOCUMENTS

| | | | |
|---|---|---|---|
| 4,409,690 | 10/1983 | Gess | 623/6 |
| 4,576,607 | 3/1986 | Kelman | 623/6 |
| 4,888,014 | 12/1989 | Nguyen | 623/6 |
| 5,141,507 | 8/1992 | Parekh | 623/6 |

FOREIGN PATENT DOCUMENTS

| | | | |
|---|---|---|---|
| 0331457 | 9/1989 | European Pat. Off. | 623/6 |
| 0438043 | 7/1991 | European Pat. Off. | 623/6 |

OTHER PUBLICATIONS

America Medical Optics Intraocular Lenses Fall '85 Brochure.

Primary Examiner—Randall L. Green
Assistant Examiner—Mary Beth O. Jones
Attorney, Agent, or Firm—Poms, Smith, Lande & Rose

[57] ABSTRACT

An intraocular lens includes an optic body and a pair of cantilevered spiral support members or haptics extending outwardly from a peripheral portion of the optic body. The haptics are formed as portions of an elongate cylindrical body. A method of making the haptics is disclosed which allows the haptic to be of variable cross sectional area, to be aplanar, and to include bends and curves, for example, without introducing undesirable molecular level changes or damage into the material of the haptic, which molecular level changes result in conventional haptics undesirably having a memory of their former shape and resulting dimensional changes (creep) of the conventional haptics over time.

23 Claims, 3 Drawing Sheets

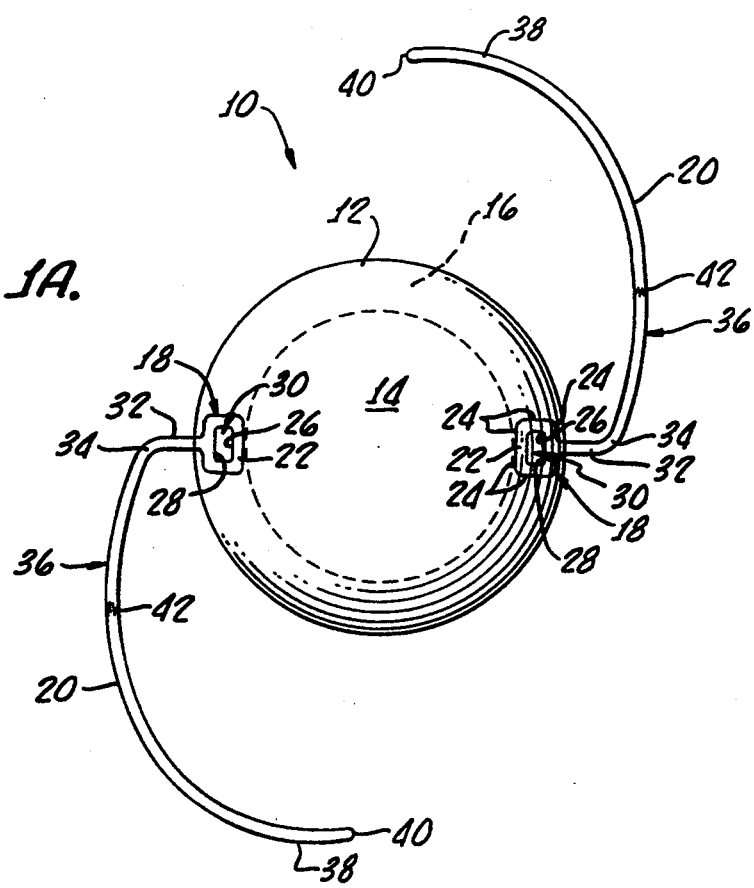
FIG. 1A.
FIG. 1B.
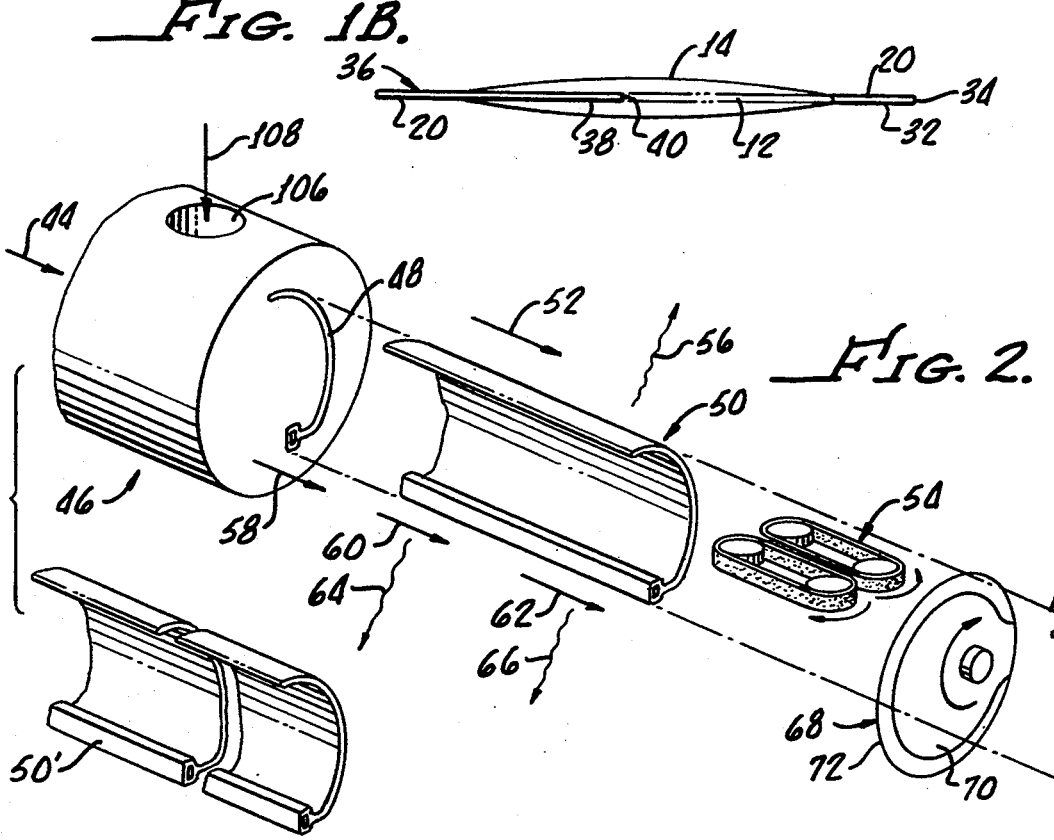
FIG. 2.

INTRAOCULAR LENS WITH IMPROVED CYLINDRICAL HAPTIC

BACKGROUND OF THE INVENTION

1. Field of the Invention

The present invention relates to intraocular lens. More particularly, the present invention related to intraocular lens having an outwardly extending elongate supporting body, or haptic, which is formed from an elongate cylindrical body. Still more particularly, the present invention relates to such a haptic, and to a method of making the haptic.

2. Related Technology

A conventional intraocular lens includes a principal refractive body, known as the lens optic, and one or more support structures for positioning and retaining the lens optic in a generally centered position within the anterior or posterior chamber of the eye. These support structures are generally elongate, filamentary-like structures, and are commonly referred to as "haptics". The haptics of an intraocular lens may be integral with the lens optic, or more commonly, are manufactured separately of the same or a different material than that which is used to make the lens optic. Commonly, the lens optic is molded about a head portion of the haptic which has securement features designed to mechanically engage with the material of the lens optic in order to provide a permanent and solid attachment of the haptic and optic one to another. Alternatively, a proximal end portion of the haptic may be adhesively secured, heat staked or otherwise fastened into an aperture of the optic body.

An important goal for intraocular lens designs is to minimize trauma to the eye when the lens is inserted through a surgical incision. Accordingly, an effort is made to ensure that the incision in the eye is kept to a small size. Also, biologically inert materials are used for the lens optic and the haptics. Additionally, the physical proportions of the lens and haptics are chosen so that the lens when resident in the eye does not interfere with, irritate, or damage the delicate tissues of the eye. On the other hand, the lens and haptics must be such that the lens optic is well supported and centered in the eye. Shifting about of the lens would be very distracting to the patient, and centration of the lens could be lost were the shifting to be of sufficient magnitude.

However, the characteristics for a material which makes it desirable for a lens optic frequently makes it undesirable for a lens haptic. The converse is also true of material selected for making of the haptics for the most part. Consequently, conventional intraocular lens are frequently made of two different materials. The lens optics are frequently made of polymethylmethacrylate (PMMA). This material is rather rigid, is easily cast or machined to shape, is biologically inert, and has excellent refractive and other optical properties for its function as a lens. Another material which is not rigid, and which is used to form flexible lenses which may be rolled or folded to ease their insertion into the eye via an incision which may be smaller than the size of the unconstrained lens, is silicone. This material has acceptable optical properties and does provide a lens with the possibility of reducing the incision size required for its insertion.

On the other hand, PMMA is rigid and in its ordinary material condition is too brittle and stiff for use in making a haptic. That is, the manipulations, and folding, for example, which a haptic must endure during the surgical insertion of the lens into the eye are too much for this relatively rigid and somewhat brittle material to endure. Moreover, elastomeric materials, such as silicone do not perform well as a haptic because they are too flimsy. Except in a broad flange configuration of lens design, which is not as desirable as the lens designs using cantilevered spiral filamentary haptics, silicone does not provide an acceptable support to the lens optic. In other words, haptics must be simultaneously pliant enough to avoid damage to delicate eye tissue and to allow deformations of the haptics during surgical implantation of the lens, and at the same time be rigid enough to act as a support structure.

The result has been an evolution toward multi-piece lenses with elongate cantilevered spiral filamentary haptics. The material of the haptics is generally polypropylene in a filamentary form. The filamentary polypropylene haptics are staked, bonded, embedded by molding the optic around a head portion of the haptic, or are otherwise secured to the lens optic. Some haptics are formed with various anchor or head features which assist their securement into the lens optic at a peripheral part thereof. U.S. Pat. Nos. 4,880,426; 4,8894,062; 4,790,846; 4,888,013; and 4,978,354; disclose lens and haptic designs which are conventional.

Nevertheless, and even in view of the numerous intraocular lens designs with their various optic and haptic designs which are conventional and known, there still exists a desire and a need for improved intraocular lens with improved haptics having better physical properties, improved handling qualities during surgical implantation, decreased costs of manufacture, eased quality control in manufacture, improved flexibility in the design of the haptic resulting from its method of manufacture, and other considerations which bear upon the overall utility of the lens and haptic combination as it is made available to the physician and patient.

SUMMARY OF THE INVENTION

In view of the deficiencies of the conventional intraocular lens and haptics for these lens, the present invention provides an intraocular lens with a lens optic, a cantilevered elongate lens haptic extending outwardly on the optic, the lens haptic being formed as a section of an elongate cylindrical body, and the haptic further including a pair of opposite surface portions which are portions of said elongate cylindrical body.

Further, the present invention provides a haptic for an intraocular lens which is formed as a section of an elongate cylindrical body, and which includes opposite surface portions which remain surface portions of the elongate cylindrical body. In other words, even if the haptic is a planar, so that in elevation view the haptic includes bends, curves, changes in section area, and other departures from a planar, sheet-like, or filament-like configuration, these deviations are accomplished by forming a section of the elongate cylindrical body so that the opposite surfaces of the body which become opposite surfaces of the haptic are surface portions of an elongate cylinder, and remain such cylindrical surface portions.

Additionally, the present invention provides a method of making an intraocular lens haptic, and an intraocular lens having such a haptic, which haptic is formed as a section of an elongate cylindrical body.

An advantage of the present invention resides in the making of the elongate cylindrical body using an extrusion process, which may include coextrusion in order to color a portion of the haptic, or to provide as an integral body a haptic including different polymer or copolymer materials having physical properties advantageous for the particular portions of the haptic where these materials are disposed in the coextrusion process.

Further as part of or subsequent to the extrusion step, the formation of the elongate cylindrical body can optionally include a molecular orientation step which improves the physical properties of the entire elongate body.

Formation of a haptic from the elongate cylindrical body is preferably accomplished without alteration of the shape of the portion of the elongate body with respect to its original cylindrical configuration. Consequently, molecular orientation alterations are not introduced into the haptic by manufacturing steps subsequent to extrusion and the optional molecular orientation step. Nevertheless, the invention provides for the formation of haptics which in elevation view have variations in thickness, bends, curves, aplanar shapes, and enlarged head or foot portions of the haptic to facilitate increased engagement surface area, for example, between the haptic and a lens optic, or between the haptic and eye tissues which support the haptic.

These and additional objects and advantages of the present invention will be apparent from a reading of the following detailed description of a non-limiting exemplary preferred embodiment of the invention, taken in conjunction with the appended drawing Figures, which are briefly described immediately below.

DESCRIPTION OF THE DRAWINGS

FIG. 1A depicts in plan view an intraocular lens including a pair of cantilevered spiral haptics;

FIG. 1B provides an elevation view of the intraocular lens seen in FIG. 1;

FIG. 2 schematically depicts a step in the manufacture of the lens seen in FIGS. 1 and 2;

DESCRIPTION OF EXEMPLARY PREFERRED EMBODIMENTS

Figure 3:
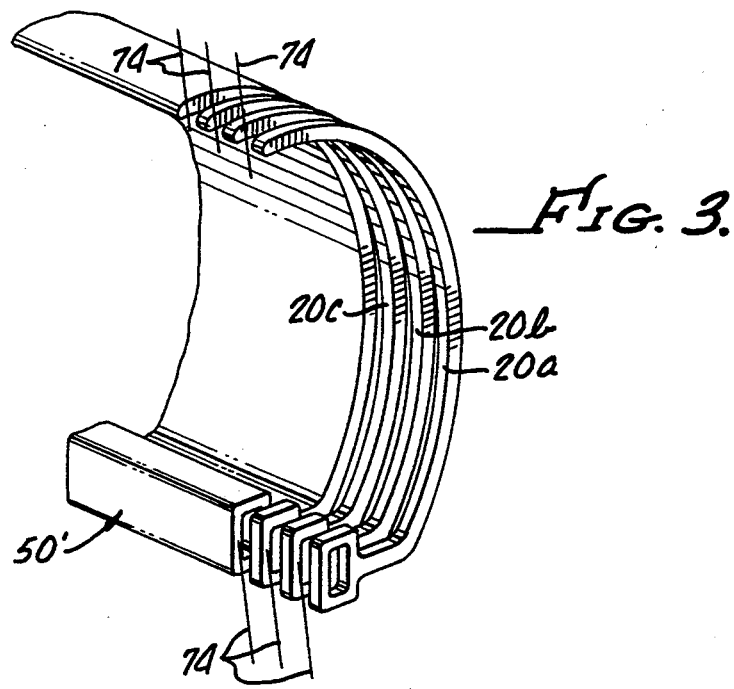
FIG. 3 provides a perspective view of a work piece resulting from the manufacturing step depicted in FIG. 2, and also depicts subsequent steps in the manufacturing process.

FIGS. 1A and 1B in conjunction depict respective plan and elevation views of an exemplary intraocular lens 10 which includes a refractive optic body, generally referenced with the numeral 12. This optic body 12 includes a central optic portion 14 through which light passes to the patient's retina when the lens is implanted in an eye. This optic portion 14 is ordinarily made with selected diopter strengths in order to provide the corrective power required to give the patient good vision after the removal of the patient's natural lens during a cataract surgery, for example. A circumferential peripheral portion 16 surrounds the optic portion 14 and is integral therewith.

Embedded in this peripheral portion 16 at a head portion 18 of each is a pair of haptics, each generally referenced with the numeral 20. These haptics are embedded into the material of the optic body by molding the material in a semi-liquid state about the pre-placed haptics. A pre-formed multi-part separable mold, along with an injection molding press may be used in an operation performing this embedding and molding step. As mentioned, these haptics each include a head portion 18 which includes structural features mechanically interlocking the haptic with the peripheral portion of the lens 10. For example, the haptics illustrated include an enlarged head feature 22 which in plan view is non circular to define plural external shoulders 24 for engagement with the surrounding material of the optic body. Also, this head feature 22 defines a non circular through hole 26 internally defining additional corners 28 which are interlocked with the material of the optic body.

The optic body material when molded about the head portions 18 of the haptics 20 flows through the holes 26 to form a bar 30 cooperating with the head portion 18 to resist torque on the haptic which could rotate the haptic in the material of the optic body. Also, as will be seen, the head portion 18 of the haptics when viewed in elevation defines additional corners and exterior features which further assist in securing the haptics into the material of the optic body.

Further viewing FIG. 1, the haptics 20 are seen to include a proximal stem portion 32 extending from the head portion outwardly of the material of the optic body 12. This proximal stem portion 32 leads to a proximal curve portion 34 of the haptic which turns toward a spirally extending shaft portion 36 of the haptic. This shaft portion 36 extends to a foot portion 38 of the haptic, at which the haptic will engage and be supported by the surrounding tissues of a patient's eye when the lens 10 is implanted in the anterior or posterior chamber of the eye. Foot portion 38 terminates at a distal end 40. Along the length of the haptic 20, intermediate of the head feature 22 and distal end 40, and as illustrated, intermediate of the proximal curve portion 34 and the foot portion 38, the haptic 20 includes a transition zone 42. This transition zone 42 may connotate a change of color for the material of the haptic. For example, the transition zone 42 may connotate a change from clear or colorless material for the proximal portions of the haptic 20 to colored material for the distal portions thereof. For example, the distal portions of the haptic may be made of colored material which is blue or green, for example, in order to ease visual identification, tracking, and manipulation of the haptics during the implanting surgical procedure. On the other hand, the clear or colorless proximal portions of the haptic 20 improve the appearance of the lens and possibly reduce glare which could be caused by colored anchor features in the lens optic.

On the other hand, the transition zone 42 may denote a change in the material properties of the haptic 20 instead of or in addition to a change in color of this material. As will be seen, the present invention allows the haptic 20 to be made of a single piece, and yet include proximal and distal portions which are of differing physical properties. This difference in physical properties may be accomplished by making the proximal and distal portions of the haptics of differing polymer or copolymer materials, or of copolymers having a differing mix of the copolymer constituents in the respective proximal and distal portions of the haptics, so that differing physical properties can be achieved in these haptic portions. For example, and without limitation, the physical properties which desirably may be varied in the portions of the haptics include such factors as hardness (durometer) of the material, its elasticity (Young's modulus), yield strength, tensile strength, softening temperature, molecular weight, brittle fracture, and elastic memory characteristics. All of these factors, and others, may be varied by selection of the polymer or copolymer material from which the haptics and their respective distal and proximal portions are made. As will be seen, the present invention allows the haptics 20 to be made in a single piece and display differing physical properties in the distal and proximal portions thereof, if desired.

Viewing FIG. 2, a step in the manufacturing process for the haptics 20 is schematically depicted. This manufacturing process includes the delivery of polymer material, represented by the arrow 44, in a heated, masticated, and molten semi-liquid condition to an extrusion die 46. The term semi-liquid is used herein to denote the non-Newtonian, highly viscous condition of most polymer materials as extruded. The delivery of the polymer material 44 to extrusion die 46 may be achieved with the use of a single or dual screw extruder, for example. Alternatively, a mass of heated polymer material may be delivered to the die 46 under pressure created by a ram extruder. The die 46 internally defines a flow path, an inlet opening of which is not visible in the drawing Figures, and an outlet opening 48 of which has a desired initial shape for the polymer product which is to be produced by the extrusion process.

Regardless of the means by which the flow 44 of polymer material is delivered to the die 46, this die provides an elongate polymer extrudate, which is referenced with the numeral 50. As will be seen this extrudate may or may not have a size when cooled which is substantially the same as opening 48. However, initially upon its exit from the die 46 (which is indicated by the arrow 52) the molten extrudate has the shape of opening 48. If the finished extrudate is to have a size when cooled which is substantially the same as the opening 48, then the extrudate is advanced away from die 46 at a smooth constant speed which is substantially the same as the rate of exit from the die 46 of the molten polymer material 44. In other words, the extrudate is neither pulled out nor retarded so as to cause a back up of molten polymer just outside of the die 46. This advancing of the extrudate 50 is achieved by use of a capstan device, which is generally referenced with the numeral 54. For example, and without limitation, the capstan device 54 may be of a caterpillar or tractor design. Alternatively, the capstan 54 could be of a belt-wrapped wheel design. The capstan 54 is speed controlled to effect a controlled smooth advancement of the extrudate 50. While this smooth continuous withdrawal of extrudate is continuing, the extrudate is cooled, as is represented by arrow 56. While this cooling of the extrudate may be achieved by simply allowing the molten polymer to give up heat to the ambient air, more preferably, the cooling is effected by directing a flow of cooling air or water onto the extrudate beginning a short distance from the die 46. Alternatively, the extrudate 50 may be advanced into a cooling bath of water. The cooled extrudate is sufficiently shape-retaining that the capstan 54 can engage the extrudate 50 without distorting it from the shape established by the die 46.

Alternatively, the extrudate 50 may be pulled and stretched even as it is progressively cooled. This alternative stretching-while-cooling method of forming the extrudate 50 is represented in FIG. 2 with movement arrows 58, 60, and 62. These arrows are of progressively longer length because of the speed of advance of the extrudate 50 increases progressively as it stretches. The progressive cooling of the extrudate as it is stretched is represented with heat arrows 64, and 66. This progressive cooling may be carried out with sequential air or water sprays spaced along the length of the extrudate 50 as it advances away from the die 46.

Subsequently, in order to facilitate ease of further handling of the extrudate 50, it is cut into selected lengths, indicated with the numeral 50', by use of an automatic knife 68. This automatic knife 68 includes a somewhat circular blade 70 with a spiral knife edge 72. Periodically, this knife blade 70 is very rapidly advanced from rest through a complete rotation and to rest. The spiral knife edge 72 cuts through the extrudate 50 without the necessity to stop the extrusion process, and yet provides a substantially perpendicular cut end at the opposite ends of the work pieces 50'.

Those ordinarily skilled in the pertinent arts will recognize that the progressive stretching of the extrudate 50 may require the use of two capstans operating at differing speeds so that the differential in their speeds represents a stretching of the extrudate. In this latter case, the extrudate is cooled sufficiently before encountering the first capstan that it will withstand the handling and forces necessary for its stretching as it progresses to the second capstan. Alternatively, the extrudate may be cooled, and stretched in a separate operation possibly including reheating of the extrudate.

Those familiar with the pertinent arts will also recognize that the extrusion process itself results in a favorable molecular structure for the extrudate 50. Generally, the combination of pressure and viscosity forces on the molten polymer 44 results in a packed molecular structure, which may be amorphous, semi-crystalline, or a mix of amorphous and crystalline. The result is an extrudate with good physical properties which are highly consistent within a manufacturing run and from one manufacturing run to the next. However, if the extrudate 50 is stretched as indicated in FIG. 2, several of the physical properties of the material can be improved. Among these improved physical properties are tensile strength, and elongation before separation under tensile force.

Still considering FIG. 2, it will be seen that the extrudate work piece 50' is an elongate cylindrical body in the classical sense of the word, "cylindrical". That is, the extrudate 50 is not a right circular cylinder, but is a body bounded by two parallel planes (the cut ends of the extrudate work pieces) and by a line tracing a closed curve perpendicular to the end planes.

FIG. 3 illustrates that the work piece 50' may be cut successively at spaced apart parallel cutting planes 74 each perpendicular to the length of the extrudate work piece 50' in order to produce plural haptics 20a, 20b, 20c, etc. Each haptic 20 is of a uniform thickness, and the thickness of the haptics can be varied from one to another to meet particular requirements of a patient or size of intraocular lens, for example.

Figure 4A:
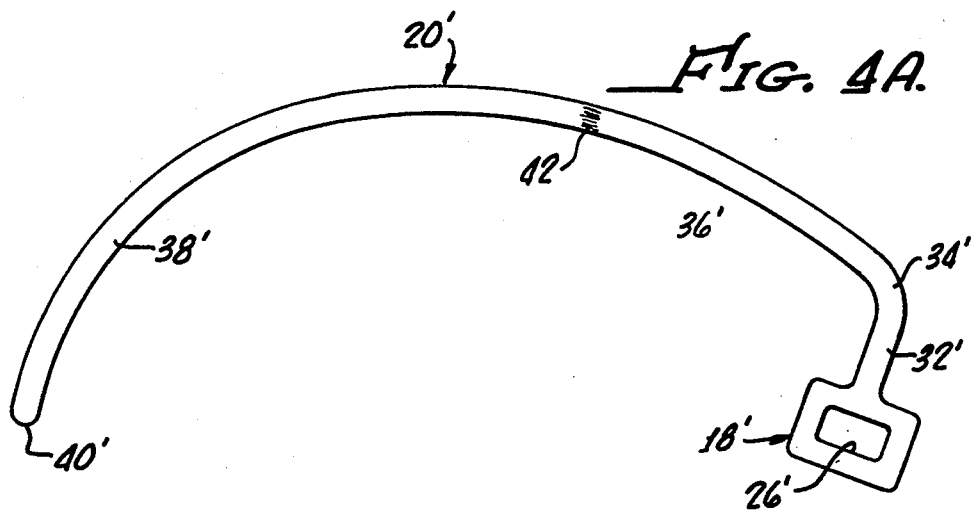
FIG. 4A provides a respective plan view of an alternative configuration of haptic which may be produced from the same work piece depicted in FIG. 3.
Figure 4B:
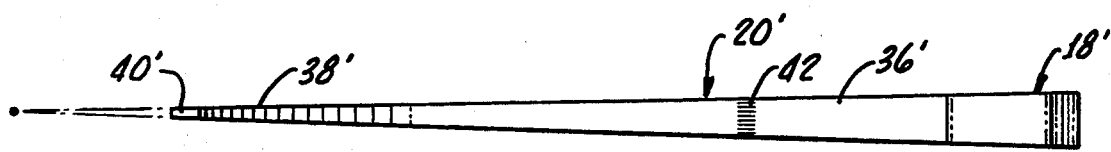
FIG. 4B provides an elevation view of the alternative configuration shown in FIG. 4A.

FIGS. 4 provide plan and elevation views of an alternative embodiment of the haptic according to the present invention. In order to obtain reference numerals for use in describing the structure depicted in FIG. 4, features which are analogous in structure or function to that described above is referenced with the same numeral used above, and with a prime added thereto. The haptic 20' depicted in FIGS. 4 can be made from the same work piece 50' depicted and described above by making successively oppositely angulated cuts across the work piece 50'. These cuts are angulated with respect to the length of the haptic which is to be formed. More particularly with respect to the geometry of the cuts made to define the haptics of FIGS. 4, these cuts in the work piece 50' are made at successively oppositely angulated planes which intersect to define a line segment disposed outside of the work piece and generally perpendicular to a length dimension of the haptic. This length dimension is generally defined as a line connecting the distal end 40' and the most distant point of the head 22'. In plan view the haptic of FIGS. 4 looks just like the haptic of FIGS. 1-3. However, the differences between the structure depicted in FIGS. 4 and that of FIGS. 1-3, is quickly apparent from a consideration of FIG. 4B. The haptic of FIGS. 4 is tapered uniformly throughout it length from the head end 22' to the distal end 40'. The cutting planes intersect at a vistal point seen in FIG. 4B. Thus, the line of intersection is perpendicular to the length of the haptic. It follows that every other piece cut from the work piece 50' is thicker at its head end 22' than at the distal end 40'. These pieces form the haptics 20', while the oppositely angulated pieces cut from work piece 50' are preferably not used as haptics. Alternatively, the cutting plane intersection line may be angulated relatively to or parallel to the length line of the haptic.

Advantageously, the haptics 20' include an enlarged or thickened head portion 22, which assists in securely anchoring the haptics in the peripheral portion of a lens optic at a later stage of manufacture. Also, the tapering stem, proximal curve, and shaft portions 32', 34', 36', leading to the tapering and smaller foot portion 38', assists in providing a haptic with sufficient strength to perform its support function, but with sufficient pliability to improve patient comfort. Also, the tapered design of the haptics depicted in FIGS. 4 provides improved strength for the haptic in the proximal curve area where bending and torquing stresses are greatest during surgical implantation. Consequently, the haptics 20' according to the embodiment of FIGS. 4, better withstand the rigors of implantation with a reduces chance of damage to the intraocular lens.

Figure 5A:
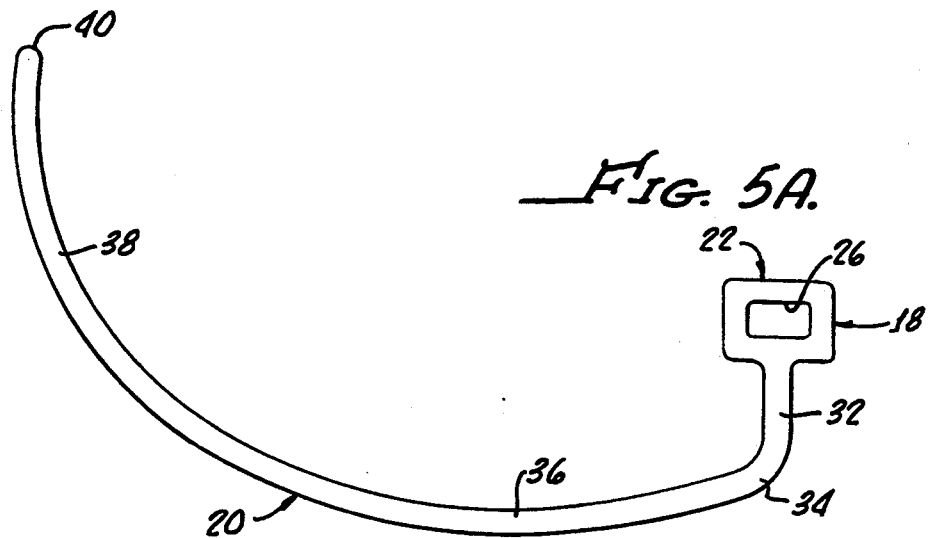
FIG. 5A provides a plan and view of yet another alternative configuration of haptic which may be produced from the work piece of FIG. 3.
Figure 5B:
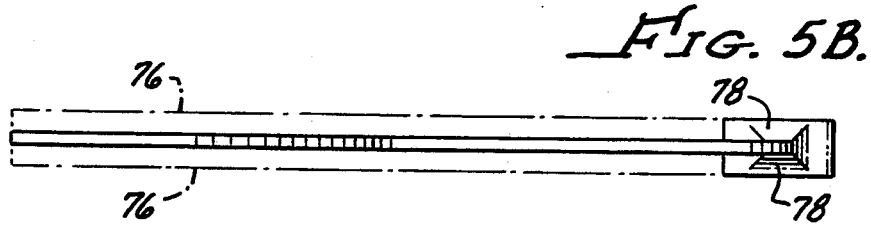
FIG. 5B provides an elevation view of the alternative configuration shown in FIG. 5A.

Yet another alternative embodiment of haptic may be formed from the work piece 50', and is depicted in FIGS. 5. In FIGS. 5, features analogous in structure or function to those depicted above are referenced with the same reference numeral. That is, the reader by now will recognize similarities and distinctions without the necessity of using primes on the reference numerals. Again, this alternative embodiment looks just like the embodiments of FIGS. 1-4 in plan view. However, in elevation view, as is seen in FIG. 5B, it is seen that this embodiment of haptic includes an enlarged head portion 22, a tapering proximal stem and proximal curve portions 32, 34, and a relatively thinner shaft portion of uniform thickness. In elevation view the shaft portion 36 is centered on the head portion 22. This configuration of haptic offers the advantages of an enlarged head and strengthened proximal curve and stem portions, while also offering an improved suppleness and flexibility for the shaft portion 36 of the haptic.

The haptic of FIGS. 5 is made by making parallel cuts across the work piece 50', with the thickness of the pieces cut off approximating the thickness of the head of the finished haptic. Subsequently, side portions indicated at 76 are removed and the removal of material is tapered out or blended at 78 as the head 22 is approached to provide the tapering proximal curve 34 and stem 32 portions of the haptic 20.

Figure 6:
FIG. 6 provides elevation view of an additional alternative configuration of haptic which may both also be produced from the work piece illustrated in FIG. 3.

Another alternative embodiment of haptic which may also be produced from work piece 50' is depicted in FIG. 6. This embodiment also appears the same in plan view as the embodiments of FIGS. 1-5. The embodiment of FIG. 6 is similar to that of FIG. 5, with the exception that the haptic shaft is offset to the side of the head 22. This haptic is produced by the same method as the embodiment of FIG. 5, with the exception that material is removed from only one side of the haptic. This embodiment offers the advantages of having the lens axially displaced from the foot portions 38 of the intraocular lens haptic along the visual axis. Accordingly, the physician is offered greater flexibility in placement of the lens optic 12 with respect to the retina, and with respect to the particular anatomy of various patients and their eye tissues which surround and support the intraocular lens 10 in use.

Figure 7:
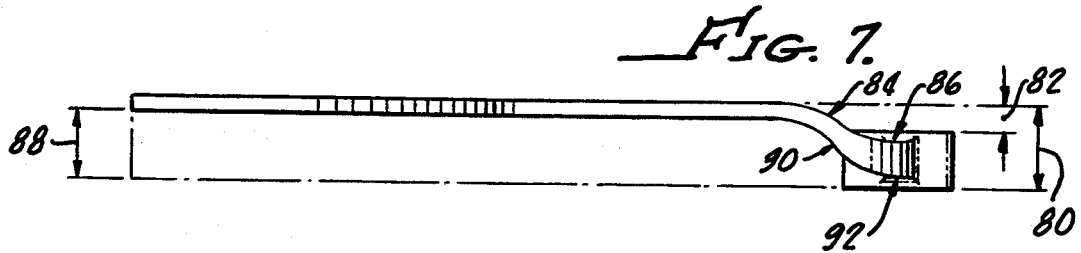
FIG. 7 provides an elevation view of another alternative configuration of haptics which may also be produced from the work piece illustrated in FIG. 3.

FIG. 7 depicts another alternative embodiment of the invention which makes clear that the present invention is not limited to making haptics with haptic shaft portions in the plane of, or bounded by the edge planes of, the haptic head. That is, a slice of material removed from the work piece 50' may be thicker than the head portion, and the head portion and haptic shaft portions may be subsequently reduced in thickness to provide a haptic shaft which includes bends, curves, and shaft portions lying outside of the bounds of the haptic head in elevation view.

Without belaboring the description of the making of the embodiment of FIG. 7, a relatively thick slice (indicated by numeral 80) is removed from the work piece 50'. On one side near the head portion, material is removed from the side of the slice of material at 82. An outwardly convex curve 84 is formed at the approach of the shaft of the haptic to the proximal curve 34 and stem 32 portions. As indicated at 86, a blend to the head portion 18 of the haptic is provided. On the other side of the haptic, material is removed from the work piece slice at 88 extending all the way along the length of the haptic shaft toward the head. At 90 an outwardly concave curved surface is provided to define a side surface on the haptic opposite the curved surface 84. Again, at the approach to the head portion 22, a blend is provided at 92.

The alternative embodiment of FIG. 7 is exemplary in the extreme. Any number of alternative configurations of haptic may be formed which all appear identical in plan view because they are fashioned from slices of the elongate cylindrical work piece 50'. On the other hand, these haptics in common with the haptics of FIGS. 1-6, retain their nature as having edge surfaces which are surface portions of the cylindrical work piece from which they are formed.

Returning now to a further consideration of FIG. 2, it is seen that the extrusion die 46 includes a secondary polymer material inlet, referenced with the numeral 106. This inlet 106 communicated with the same flow path which receives material flow 44 so that polymer material (indicated by arrow 108) introduced into the inlet 106 flows from outlet 48 adjacent the distal end of the haptic when viewed in plan. This material 108 somewhat mixes with the material 44 within the extrusion die 46 in view of the pressure and viscosity forces effective on the two flows 44 and 108 to define the transition zone 42. On the other hand, the materials 44 and 108 remain separate and distinct from one another in their respective proximal and distal end portions of the haptic on opposite sides of the transition zone 42. Those ordinarily skilled in the pertinent arts will recognize the described process as being based on principles of coextrusion.

The location of the transition zone along the haptic 20, that is, the size of the proximal and distal portions of the haptic which are formed of material from flow 44, and from flow 108, are selectively variable by variation in the respective mass flow rates of these two flows of material. As a result of the mixing and compatibility of the materials in transition zone 42, the haptics 20 are of a single piece but may have differing colors, or material properties, or both, in the respective end portions of the haptic.

A particular advantage that derives from this aspect of the invention is the ability for physicians and designers of intraocular lenses to select a strong comparatively rigid polymer material for the proximal portion of the haptic where bending and torsion forces are the highest during implantation. At the same time these physicians and lens designers may also select a comparatively softer and more pliable polymer material for the distal portion of the haptic so that compression force levels and compliance of the haptic can be tailored to allow easy insertion of the intraocular lens through an eye incision. As a result, a single-piece dual-material haptic according to the invention can provide the comfort, lens support, and centration of the lens optic which is so important to patient satisfaction.

Also importantly, the dual-material nature of the haptics of the present invention is achieved without welding, adhesive bonding, or heat processing of the haptic material after the extrusion operation. Thus, the risks of molecular level alterations of the material of the haptic, of degradation of the material by welding operations, and the possibility of adhesive or solvent residues which could later be released from the lens within a patient's eye are eliminated by the present invention.

Still further, the embodiments of the haptic illustrated in FIGS. 5–7, and particularly FIG. 7, provide the physician and lens designer with the possibility of making haptics with shaft portions lying outside of the plane of the lens. That is, the shaft portion of the haptic may include parts thereof which are outside of the plane of the lens, or outside of the boundary planes of the head portion of the haptic, which includes bends and curves, and which does not rely on heat distortion of the material of the haptic in order to achieve these haptic configurations. Accordingly, the material of the haptic is free of molecular level material memory of its former configuration. With conventional heat-deformed haptics, such molecular level material memory of a former configuration can result in the haptics over time creeping back toward their pre-deformation configuration with resultant loss of lens centration, axial lens shift, or discomfort for the patient.

While the present invention has been depicted, described, and is defined by reference to particularly preferred embodiments of the invention, such reference does not imply a limitation on the invention, and no such limitation is to be inferred. The invention is capable of considerable modification, alteration, and equivalents in form and function, as will occur to those ordinarily skilled in the pertinent arts. For example, the haptics 20 do not necessarily need to include an enlarged head portion 22. The head portion of the haptics could be made the same or a similar cross sectional shape as the shaft portion 36 of the haptic, for example. This haptic head portion could then be glued, welded, or locked in some other way into an aperture or other receiving feature of the optic body 12. Alternatively, the extended haptic could be simply bonded to a peripheral surface of the lens optic. Accordingly, the depicted and described preferred embodiments of the invention are exemplary only, and are not exhaustive of the scope of the invention. Consequently, the invention is intended to be limited only by the spirit and scope of the appended claims, giving full cognizance to equivalents in all respects.

What is claimed is:

1. An intraocular lens including an optic body and at least one haptic securing to said optic body and extending outwardly therefrom, said haptic comprising a generally transverse section of a cylindrical body, and said haptic further including a surface portion which is a surface portion of said cylindrical body; and wherein said haptic includes a head portion at a proximal end, said head portion including shoulders disposed generally axially of said intraocular lens, and said optic body engaging said shoulders to anchor said haptic head portion within said optic body.

2. The intraocular lens of claim 1 wherein said at least one haptic includes a pair of opposite surface portions which are surface portions of said cylindrical body.

3. The intraocular lens of claim 1 wherein said at least one haptic is a unitary structure of a single piece and includes a distal portion spaced from said optic body by said proximal portion, said proximal and distal portions of said at least one haptic having differing physical properties.

4. The intraocular lens of claim 3 wherein said differing physical properties of said proximal and said distal portions includes a difference in color.

5. The intraocular lens of claim 3 wherein said differing physical properties of said proximal and said distal portions includes a difference in polymer material of said portions.

6. The intraocular lens of claim 1 wherein said at least one haptic includes an elongate shaft portion extending from said head portion and outwardly of said optic body.

7. The intraocular lens of claim 6 wherein said head portion defines a thickness dimension generally axially of said intraocular lens, said haptic shaft portion being of like thickness with said head portion.

8. The intraocular lens of claim 6 wherein said head portion defines a thickness dimension generally axially of said intraocular lens, said haptic shaft portion having a thickness dimension less than said head portion.

9. The intraocular lens of claim 8 wherein said shaft portion is tapering uniformly along a length dimension thereof from said head portion to a distal end of lesser thickness than said head portion.

10. The intraocular lens of claim 8 wherein said haptic shaft portion includes a proximal stem portion blending in thickness between said head portion and the remainder of said haptic shaft portion.

11. The intraocular lens of claim 10 wherein said haptic shaft portion is centered on said head portion in elevation view.

12. The intraocular lens of claim 10 wherein said haptic shaft portion is offset from a centered position on said head portion in elevation view.

13. The intraocular lens of claim 8 wherein said thickness dimension of said head portion is defined by a pair of generally parallel boundary planes axially spaced apart at respective sides of said head portion, said shaft portion in elevation view traversing at least one of said pair of boundary planes.

14. An intraocular lens including an optic body and at least one haptic securing to said optic body and extending outwardly therefrom, said haptic comprising a generally transverse section of a cylindrical body, and said haptic further including a surface portion which is a surface portion of said cylindrical body; wherein said haptic is a unitary structure of a single piece and includes a proximal portion adjacent said optic body and a distal portion spaced from said optic body by said proximal portion, said proximal and distal portions of said haptic having differing physical properties; wherein said haptic includes a transition zone in which said physical properties from those of said proximal and distal portions are mixed.

15. The intraocular lens of claim 14 wherein said transition zone is defined while a polymer material of said haptic is substantially of a uniform temperature and without thermal or chemical welding, whereby the molecular structure of said haptic polymer material is not degraded or altered by welding heat or chemicals.

16. An intraocular lens comprising:

an optic body having a central optic portion and a peripheral portion circumscribing said central optic portion, said peripheral portion embracing a support haptic to anchor the latter within said optic body;

said support haptic including a head portion embedded within said peripheral portion of said optic body, a proximal stem portion extending from said head portion and outwardly of said optic body, a proximal curve portion extending from said stem portion, and an elongate shaft portion extending from said proximal curve portion, said shaft portion defining a distal end and a distal foot portion adjacent said distal end and supportingly engageable with surrounding eye tissues;

said haptic being a section of a cylindrical body and including opposite side surface portions which are surface portions of said cylindrical body.

17. The intraocular lens of claim 16 wherein said haptic further includes elongated molecular chains, said molecular chains produced by elongation of said cylindrical body.

18. The intraocular lens of claim 16 wherein said haptic shaft portion defines a thickness dimension less than that of said head portion.

19. The intraocular lens of claim 18 wherein said haptic shaft portion tapers in thickness toward said distal end.

20. The intraocular lens of claim 16 wherein said haptic includes a transition zone between said proximal curve portion and said distal end.

21. The intraocular lens of claim 20 wherein said proximal portion and said distal portion have a differing physical property.

22. The intraocular lens of claim 21 wherein said differing physical property includes a difference in color.

23. The intraocular lens of claim 21 wherein said differing physical property includes a difference in a polymer material from which said haptic is formed.

* * * * *